United States Patent
Kamibayashi et al.

(10) Patent No.: US 6,555,058 B2
(45) Date of Patent: Apr. 29, 2003

(54) APPARATUS FOR ARTIFICIAL KIDNEY, QUALITY EVALUATING DEVICE FOR DIALYZING FLUID AND DIALYZING MEANS USING THE SAME, AND FLUID CIRCUIT

(75) Inventors: Masato Kamibayashi, Kanagawa (JP); Jiro Sawamoto, Kanagawa (JP); Shinji Motoyama, Kanagawa (JP); Fumiaki Endo, Shizuoka (JP)

(73) Assignee: Asahi Medical Co., Ltd., Tokyo (JP)

( * ) Notice: Subject to any disclaimer, the term of this patent is extended or adjusted under 35 U.S.C. 154(b) by 119 days.

(21) Appl. No.: 09/742,341

(22) Filed: Dec. 22, 2000

(65) Prior Publication Data

US 2001/0005487 A1 Jun. 28, 2001

(30) Foreign Application Priority Data

Dec. 24, 1999 (JP) .......................... 11-368349

(51) Int. Cl.⁷ .............................. A61M 37/00
(52) U.S. Cl. ...................... 422/44; 604/4.01
(58) Field of Search ............. 422/44–48; 604/4.01–6.16

(56) References Cited

U.S. PATENT DOCUMENTS

| | | | |
|---|---|---|---|
| 4,844,871 A | | 7/1989 | Polaschegg |
| 5,018,527 A | | 5/1991 | Pfab et al. |
| 5,810,759 A | * | 9/1998 | Merz ........................ 422/44 |
| 5,957,880 A | * | 9/1999 | Igo et al. ................... 422/44 |
| 6,117,099 A | * | 9/2000 | Steuer et al. ............... 422/44 |
| 6,336,910 B1 | * | 1/2002 | Ohta et al. ............. 128/DIG. 3 |

FOREIGN PATENT DOCUMENTS

| | | |
|---|---|---|
| JP | 62-270136 | 11/1987 |
| JP | 64-50948 | 2/1989 |
| JP | 9-10300 | 1/1997 |
| JP | 9-10301 | 1/1997 |
| JP | 9-19497 | 1/1997 |

OTHER PUBLICATIONS

Kato, *Journal of Japanese Society of Nephrology*, vol. 29, pp. 1249–1259, 1987.
Okamoto, *Hiroshima Journal of Medical Sciences*, vol. 35, No. 4, pp. 1031–1081, 1987.
Jacob et al., *Kidney International*, vol. 18, pp. 505–509, 1980.
Oyama et al., *Journal of Japanese Society for Dialysis Therapy*, vol. 29, pp. 29–35, 1996.
Nishimura et al., *Therapeutic Research*, vol. 18, No. 7, pp. 2205–2209, 1997.
Fukuyama et al., *Free Radical Biology & Medicine*, vol. 22, No. 5, pp. 771–774, 1997.

(List continued on next page.)

*Primary Examiner*—Steven O. Douglas
(74) *Attorney, Agent, or Firm*—Burns, Doane, Swecker & Mathis, LLP

(57) ABSTRACT

An apparatus which can solve the problem of participation of NO in hypotension in dialysis, hypoxia in dialysis, and the like during artificial dialysis by continuously monitoring fluctuation in a blood gas, an ionic component, or the like in body fluid such as blood and by suppressing these diseases, and quality evaluating means of an artificial dialyzer and dialyzing fluid are provided. An apparatus for an artificial kidney comprises a measurement monitor for continuously measuring nitric oxide as a component of body fluid or liquid for treatment. Further, an apparatus for an artificial kidney comprises a measurement monitor for measuring a component of body fluid or liquid for treatment, a display means for comparing a measurement measured by the measurement monitor with a control value, and when the measurement equals the control value, displays the equality, and oxygen supplying means.

13 Claims, 5 Drawing Sheets

OTHER PUBLICATIONS

Umino et al., *Journal of Japanese Society for Dialysis Therapy,* vol. 31, No. 5, pp. 933–938, 1998.

Kang et al., *American Journal of the Medical Sciences,* vol. 317, No. 1, pp. 9–21, 1999.

Madore et al., *American Journal of Kidney Diseases,* vol. 30, No. 5, pp. 665–671, 1997.

Douma et al., *Clinical Nephrology,* vol. 45, No. 5, pp. 295–302, 1996.

Yonetani, *Folia Pharmacologica Japonica,* vol. 112, pp. 155–160, 1998.

Igarashi, *Japanese Journal of Thotacic Diseases,* vol. 24, pp. 531–540, 1986.

Masuda et al., *Japanese Journal of Clinical Medicine,* vol. 49, Special Issue, Blood Purification (first volume), pp. 709–713, 1991.

Green et al., *Analytical Biochemistry,* vol. 126, pp. 131–138, 1982.

Sasaki et al., *Journal of the Japanese Society for Dialysis Therapy,* vol. 32, No. 5, pp. 363–368, 1999.

Rysz et al., *Kidney International,* vol. 51, pp. 294–300, 1997.

Amore et al., *Journal of the American Society of Nephrology,* vol. 6, No. 4, pp. 1278–1283, 1995.

Kato, *Journal of Japanese Dental Society of Anesthesiology,* vol. 25, No. 2, pp. 184–196, 1997.

\* cited by examiner

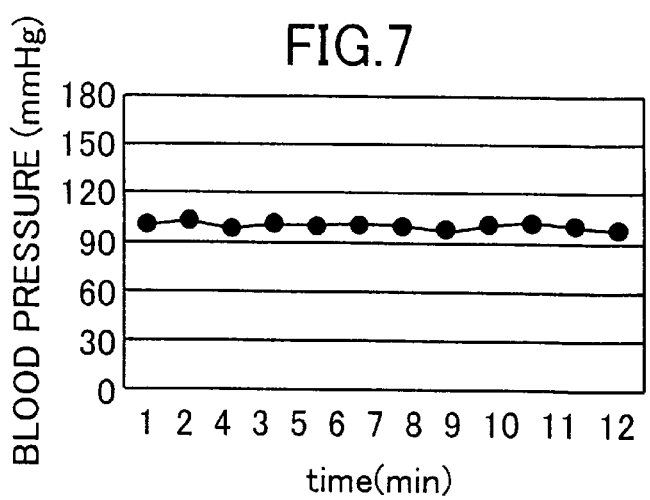
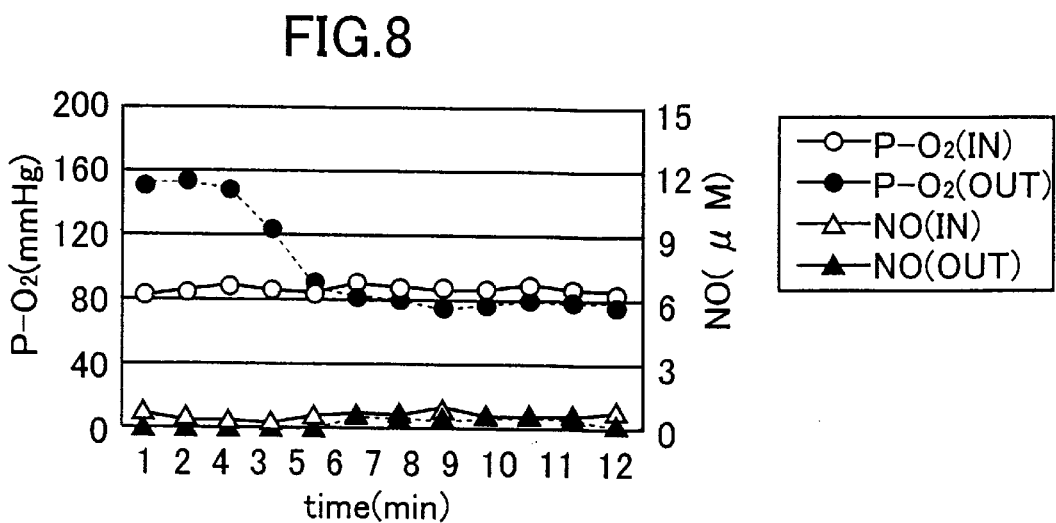
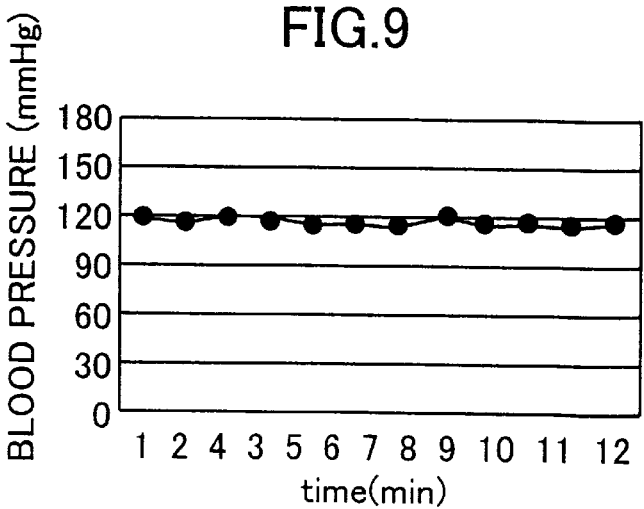

APPARATUS FOR ARTIFICIAL KIDNEY, QUALITY EVALUATING DEVICE FOR DIALYZING FLUID AND DIALYZING MEANS USING THE SAME, AND FLUID CIRCUIT

BACKGROUND OF THE INVENTION

1. Field of the Invention

The present invention relates to an apparatus for an artificial kidney for continuously measuring a component in body fluid such as blood or plasma, or liquid for treatment such as dialyzing fluid or supplementary liquid, or for measuring it and further adjusting the partial pressure of oxygen in the body fluid or in the liquid for treatment using oxygen supplying means, to a fluid circuit used in such an apparatus, and a quality evaluating device using such an apparatus for artificial kidney and its fluid circuit.

The present invention also relates to a method of preventing or treating hypotension and hypoxia associating with artificial dialysis in treatment using an apparatus for an artificial kidney by controlling partial pressure of oxygen in body fluid.

2. Description of the Related Art

Abnormal living body cases of an artificial dialysis patient include hypotension in dialysis (Mariko Kato, Journal of Japanese Society of Nephrology, Vol. 29, pp. 1249–1259 (1987)), hypoxia in dialysis where the partial pressure of oxygen in artery is decreased (Takumi Okamoto, Medical Journal of Hiroshima University, Vol. 35, pp. 1031–1081 (1987) and Jacob A. J. et al., Kidney International, Vol. 18, pp. 505–509 (1980)), and the like. It has been pointed out that decrease in the partial pressure of oxygen in the blood during dialysis (hereinafter referred to as $P_{O^2}$) is part of the onset mechanism of the hypotension in dialysis that previously described in literatures. Recently, it has been pointed out that, during dialysis, a large amount of nitric oxide (hereinafter referred to as NO) having a strong vasodilator action is produced in the blood through the stimulus of cytokine, endotoxin, or the like, which participates in the onset mechanism of the hypotension in dialysis.

For example, it is reported that, during hemodialysis, the concentration of NO and NO oxydants (hereinafter referred to as NOx) is increased, and thus, acceleration of NO production in dialysis patients is observed (Nobuo Oyama et al., Journal of Japanese Society for Dialysis Therapy, Vol. 29, pp. 29–35 (1996), Hiroe Nakazawa et al., Chiryogaku (Biomedicine and Therapeutics), Vol. 24, pp. 283–287 (1996), Masato Nishimura et al., Therapeutic Research, Vol. 18, pp. 2205–2209 (1997), Fukuyama N. et al., Free Radical Biological Methods, Vol. 22, pp. 771–774 (1997), Nobuo Oyama et al., Jin to Toseki (Kidney and Dialysis), Vol. 45, pp. 765–768 (1988), Tetsuo Unno, Journal of Japanese Society for Dialysis Therapy, Vol. 31, pp. 933–938 (1998), Ellen S. et al., American Journal of the Medical Sciences, Vol. 313, pp. 138–146 (1997), Madore F. et al., American Journal of Kidney Diseases, Vol. 30, pp. 665–671 (1997), and Douma C. E. et al., Advance in Peritoneal Dialysis, Vol. 11, pp. 36–40 (1995)). NO has physiological functions such as a strong vasodilator action. Chemically, at a high concentration, oxidation reaction of NO is rapid, while, at a steady state in blood (0.1–10 $\mu$M), NO is relatively stable (Takashi Yonetani, Folia Pharmacologica Japonica, Vol. 112, pp. 155–160 (1998)).

Attempts to prevent hypoxia during hemodialysis include a case where sodium bicarbonate dialyzing fluid having high partial pressure of carbon dioxide ($P_{CO^2}$) is used instead of acetic acid dialyzing fluid (Hideo Igarashi, Japanese Journal of Thotacic Diseases, Vol. 24, pp. 531–540 (1986)) and a case where pharmacotherapy is used (Hitoshi Masuda, et al., Japanese Journal of Clinical Medicine, Vol. 49, 1991, Special Issue, Blood Purification (the first volume), pp. 709–713), and the like. With regard to determination of NO described in the above-described publicly known literature, an indirect method which presumes the amount of NO from the amount of NOx produced, for example, the Griess method (Green L. C. et al., Analytical Biochemistry, Vol. 126, pp. 131–138 (1982) has been generally used.

To evaluate biocompatibility of a hemodialyzer using a hollow fiber membrane, a method with the amount of NO or NOx produced being an index has been conventionally reviewed. Such a method measures the amount in vitro using blood sampled intermittently (Nobuhiro Sasaki et al., Journal of The Japanese Society for Dialysis Therapy, Vol. 32, pp. 363–368 (1999), Rysz J. et al., Kidney International, Vol. 51, pp. 294–300 (1997), and Amore A. et al., The Journal of American Society of Nephrology, Vol. 6, pp. 1278–1283 (1995)). In these methods, since continuous measurement is not possible, change during hemodialysis can not be known immediately.

A method of measuring $P_{O^2}$, $P_{CO^2}$, or pH in blood passing through an extracorporeal circulation circuit using the electrode method is disclosed in, for example, JP-A-61-2867, JP-A-61-280844, JP-A-62-155834, JP-A-62-270136, JP-A-64-50948, JP-A-9-10300, JP-A-9-10301, JP-A-3-131240, and JP-A-9-19497. As an example of measurement of NO concentration in vivo using an NO electrode, there is a case of cardiac muscle tissue of a rabbit under anesthesia where NO concentration and partial pressure of oxygen in artery are simultaneously measured (Seiichi Kato, The Journal of Japanese Dental Society of Anesthesiology, Vol. 25, pp. 184–196 (1997). However, no case is known where such measurement is applied to an apparatus for an artificial kidney and to a fluid circuit.

SUMMARY OF THE INVENTION

In view of the above, the present invention is made to solve the problem of participation of NO in dialysis induced hypotension, hypoxia in dialysis, and the like during artificial dialysis, and an object of the present invention is to provide an apparatus which can continuously monitor fluctuation in a gaseous component, an ionic component, or the like in body fluid such as blood and can suppress these diseases. Another object of the present invention is to provide quality evaluating means of an artificial dialyzer and dialyzing fluid using such an apparatus.

The inventors of the present invention vigorously carried out researches to solve the above-described problem, and found that to continuously measure the nitric oxide concentration in the blood circulation circuit or the dialyzing fluid circuit during dialysis, is useful to prevent hypotension in dialysis. Further, the inventors of the present invention found that, by maintaining $P_{O^2}$ in a normal range, the partial pressure of oxygen in arterial blood during dialysis, excess increase in the NO concentration in blood pointed out as participating in dialysis induced hypotension can be prevented. Further, the inventors of the present invention found that oxygen supply to arterial blood is effective in facilitating metabolism of NO in blood and in suppressing hypoxia.

The present invention is implemented by the following structures.

(1) An apparatus for an artificial kidney comprising a first fluid circuit for introducing body fluid into dialyzing means, dialyzing means for removing waste products from the body fluid, and a second fluid circuit for recovering the body fluid, further comprising a measurement monitor for continuously measuring at least one component of the body fluid in the first fluid circuit and/or the second fluid circuit.

(2) An apparatus for an artificial kidney as described in the above (1), wherein the component is at least one which is selected from a group consisting of nitric oxide, oxygen, nitrous acid ions, and nitric acid ions.

(3) An apparatus for an artificial kidney as described in the above (1) or (2), wherein at least one which is selected from a group consisting of the first fluid circuit, the dialyzing means, and the second fluid circuit is provided with a treatment liquid supplying device for supplying liquid for treatment.

(4) An apparatus for an artificial kidney as described in any one of the above (1) to (3), further comprising oxygen supplying means for increasing partial pressure of oxygen in arterial blood of a living body.

(5) An apparatus for an artificial kidney as described in the above (4) comprising a first fluid circuit for introducing body fluid of a living body into dialyzing means, dialyzing means for removing waste products from the body fluid, a second fluid circuit for recovering and returning the body fluid to the living body, and oxygen supplying means for increasing partial pressure of oxygen in arterial blood of the living body, characterized by further comprising a measurement monitor for continuously measuring at least one component of the body fluid in the first fluid circuit and/or the second fluid circuit, and display means for displaying the result of comparison between a measurement value measured by the measurement monitor and a desired value.

(6) An apparatus for an artificial kidney as described in the above (5), wherein the apparatus controls, linked with the display by the display means, controls the oxygen supplying means and controls the partial pressure of oxygen in the body fluid or the liquid for treatment.

(7) A method for preventing or treating hypotension and/or hypoxia associated with artificial dialysis by comprising a first fluid circuit for introducing body fluid of a living body into dialyzing means, dialyzing means for removing waste products from the body fluid, a second fluid circuit for recovering and returning the body fluid to the living body, and oxygen supplying means for increasing partial pressure of oxygen in arterial blood of the living body, by further comprising a measurement monitor for continuously measuring at least one component of the body fluid in the first fluid circuit and/or the second fluid circuit, by comparing a measurement value measured by the measurement monitor with a desired value, and by controlling the concentration of the component of the living body.

(8) An apparatus for an artificial kidney as described in any one of the above (5) to (7), wherein the oxygen supplying means is at least one which is selected from a group consisting of an air bubble type oxygenator, a membrane type oxygenator, an oxygen inhaler, an oxygen tent, an oxygen respiration synchronizer, and an oxygen concentrator.

(9) An apparatus for an artificial kidney as described in any one of the above (1) to (8), wherein the dialyzing means is a blood processor using a hollow fiber membrane and/or the liquid for treatment is dialyzing fluid.

(10) A quality evaluating device for dialyzing means comprising a first fluid circuit for introducing body fluid into dialyzing means, dialyzing means for removing waste products from the body fluid, and a second fluid circuit for recovering the body fluid, further comprising a measurement monitor for continuously measuring at least one component of the body fluid in the first fluid circuit and/or the second fluid circuit, and optional oxygen supplying means, and capable of evaluating the quality of the dialyzing means.

(11) A fluid circuit usable in an apparatus for an artificial kidney as described in any one of the above (1) to (10), comprising a measurement monitor for continuously measuring at least one component of the body fluid in the fluid circuits, and/or oxygen supplying means.

(12) A quality evaluating device for dialyzing fluid comprising a first fluid circuit for introducing body fluid into dialyzing means, dialyzing means for removing waste products from the body fluid, and a second fluid circuit for recovering the body fluid, further comprising a measurement monitor for continuously measuring at least one component of the body fluid in the first fluid circuit and/or the second fluid circuit, optional oxygen supplying means, and a dialyzing fluid supplying device for supplying dialyzing fluid to the dialyzing means, and capable of evaluating the quality of the dialyzing fluid.

(13) A method of controlling the concentration of a component of body fluid of a living body by comprising a first fluid circuit for introducing body fluid of a living body into dialyzing means, dialyzing means for removing waste products from the body fluid, a second fluid circuit for recovering and returning the body fluid to the living body, and oxygen supplying means for increasing partial pressure of oxygen in arterial blood of the living body, by further comprising a measurement monitor for continuously measuring at least one component of the body fluid in the first fluid circuit and/or the second fluid circuit, and by comparing a measurement value measured by the measurement monitor with a desired value.

(14) A method as described in any one of the above (10) to (13), wherein the oxygen supplying means is at least one which is selected from a group consisting of an air bubble type oxygenator, a membrane type oxygenator, an oxygen inhaler, an oxygen tent, an oxygen respiration synchronizer, and an oxygen concentrator.

(15) A dialyzing fluid supplying device comprising a third fluid circuit for introducing dialyzing fluid, and a fourth fluid circuit for recovering the dialyzing fluid, characterized by further comprising a measurement monitor for continuously measuring at least one component of the dialyzing fluid in the third fluid circuit and/or the fourth fluid circuit.

In the above (15), it is the apparatus for an artificial kidney as described in the above (1) which comprises the third fluid circuit for introducing the dialyzing fluid, and the third fluid circuit for introducing dialyzing fluid is a dialyzing fluid supplying circuit for supplying dialyzing fluid to the dialyzing means. The fourth fluid circuit may be a dialyzing fluid recovering circuit for recovering the dialyzing fluid from the dialyzing means. Further, in the above (15), the third fluid circuit for introducing the dialyzing fluid may be a peritoneal dialyzing fluid introducing circuit for introducing the dialyzing fluid to the abdominal cavity and dialyzing blood in capillaries in the peritoneum utilizing the peritoneum in peritoneal dialysis, and the fourth fluid circuit may be a peritoneal dialyzing fluid drain circuit for collecting waste products from the inside of the abdominal cavity to the outside of the body.

(16) An apparatus for an artificial kidney comprising a measurement monitor for continuously measuring nitric oxide as a component of body fluid or liquid for treatment.

(17) An apparatus for an artificial kidney comprising a measurement monitor for continuously measuring a component of body fluid or liquid for treatment, a display means for comparing a measurement value measured by the measurement monitor with a control value, and when the measurement equals the control value, displays the equality, and oxygen supplying means.

(18) An apparatus for an artificial kidney as described in the above (16) or (17), wherein the component is at least nitric oxide and oxygen.

(19) An apparatus for an artificial kidney as described in any of the above (16) to (18), wherein the component is at least one selected from a group consisting of, in addition to the above, nitrous acid ions, nitric acid ions, and carbonic acid ions.

(20) An apparatus for an artificial kidney as described in any one of the above (17) to (19), wherein the apparatus controls, linked with the display by the display means, controls the oxygen supplying means, and controls the partial pressure of oxygen in the body fluid or the liquid for treatment.

(21) An apparatus for an artificial kidney as described in any one of the above (17) to (20), wherein the oxygen supplying means is an oxygen inhaler or an oxygenator to the body fluid or an oxygen addition to the liquid for treatment.

(22) An apparatus for an artificial kidney as described in any one of the above (16) to (21), wherein the artificial kidney is a blood processor using a hollow fiber membrane.

(23) A quality evaluating device for evaluating the quality of a blood processor using a hollow fiber membrane which uses an apparatus for an artificial kidney as described in any one of the above (16) to (22).

(24) A quality evaluating device for evaluating the quality of dialyzing fluid as liquid for treatment which uses an apparatus for an artificial kidney as described in any one of the above (16) to (22).

(25) A fluid circuit for an apparatus for an artificial kidney comprising a nitric oxide measuring portion for continuously measuring nitric oxide as a component of body fluid or liquid for treatment.

(26) A fluid circuit for an apparatus for an artificial kidney comprising a component measuring portion for continuously measuring a component of body fluid or liquid for treatment, and an oxygen adding portion for adding oxygen to the body fluid or the liquid for treatment.

(27) A fluid circuit for an apparatus for an artificial kidney as described in the above (25) or (26), wherein the component is at least nitric oxide and oxygen.

(28) A fluid circuit for an apparatus for an artificial kidney as described in any one of the above (25) to (27), wherein the component is at least one selected from a group consisting of, in addition to the above, nitrous acid ions, nitric acid ions, and carbonic acid ions.

(29) A fluid circuit for an apparatus for an artificial kidney as described in any one of the above (25) to (28), wherein the artificial kidney is a blood processor using a hollow fiber membrane.

(30) A circuit for a quality evaluating device for evaluating the quality of a blood processor using a hollow fiber membrane which uses a fluid circuit as described in any one of the above (25) to (29).

(31) A circuit for a quality evaluating device for evaluating the quality of dialyzing fluid as liquid for treatment which uses a fluid circuit as described in any of the above (25) to (29).

BRIEF DESCRIPTION OF THE DRAWINGS

FIG. 7 is a graph of the result of measurement of the blood pressure in the measurement example of FIG. 6.

FIG. 8 is a graph of the result of still another measurement of $P_{O^2}$ and the NO concentration which is made with regard to another measurement example of Example 3.

FIG. 9 is a graph of the result of measurement of the blood pressure in the measurement example of FIG. 8.

DETAILED DESCRIPTION OF THE PREFERRED EMBODIMENTS

Figure 1:
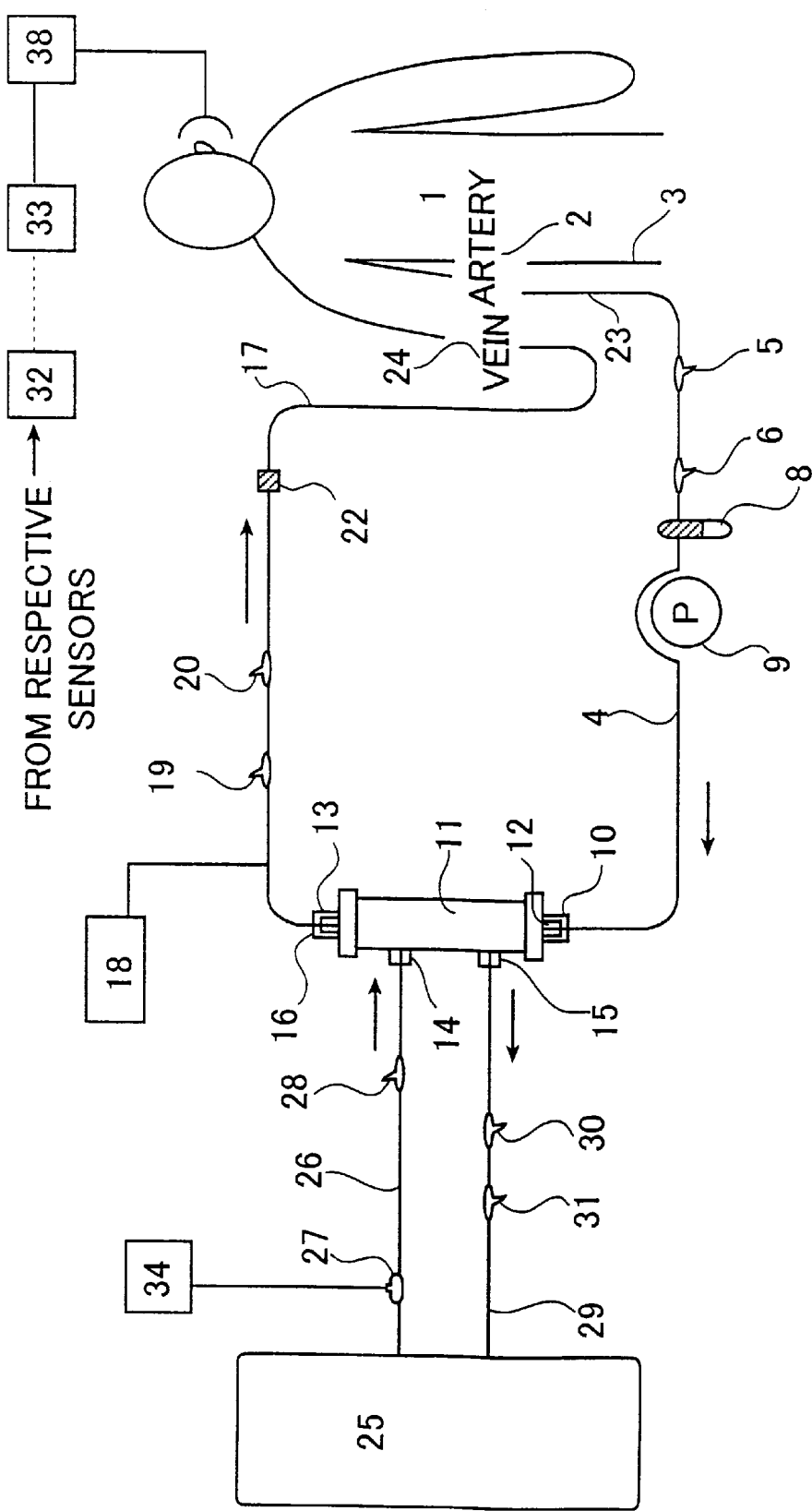
FIG. 1 is a structural view as a whole, illustrating Example 1 according to the present invention.

According to a first aspect of the present invention, an apparatus for an artificial kidney comprises a first fluid circuit for introducing body fluid into dialyzing means (dialyzer), dialyzing means for removing waste products from the body fluid, and a second fluid circuit for recovering the body fluid, and further comprises a measurement monitor for continuously measuring at least one component of the body fluid in said first fluid circuit and/or said second fluid circuit.

Body fluid as used herein means blood, plasma, hemofiltration liquid, and the like. Further, an apparatus for an artificial kidney according to the present invention may further comprise a treatment liquid supplying device. The liquid for treatment which is supplied includes dialyzing fluid for hemodialysis conventionally used in hemodialysis treatment, dialyzing fluid after passing through a hemodialyzer, supplementary liquid and substitution liquid used in hemofiltration or hemodia-filteration, peritoneal dialyzing fluid used in peritoneal dialysis, processed dialyzing fluid drained from the abdominal cavity after peritoneal dialysis, and the like.

As fluid circuits according to the present invention, there are a first fluid circuit for introducing body fluid into dialyzing means, a second fluid circuit for recovering the body fluid from the dialyzing means, a third fluid circuit for introducing dialyzing fluid, and a fourth fluid circuit for recovering the dialyzing fluid, the third and fourth fluid circuits being provided as the need arises. These fluid circuits are provided with a measurement monitor for continuously measuring at least one component of the body fluid or the liquid for treatment therein.

A fluid circuit according to the present invention is a cylindrical body, and, though it is usually a tube made of plastic, it may also be a lumen in a catheter or a syringe or the like, and may have any shape which allows the body fluid or the liquid for treatment to circulate therethrough.

A fluid circuit according to the present invention may be provided with a publicly known functional member used in various kinds of circuits, as necessary, for example: a pump for making a flow of fluid; an air chamber for capturing air bubbles in the circuit; an air bubble detecting portion for detecting air bubbles; a fluid inlet, a fluid outlet, a supplementary liquid line connecting port, and a mixed injection port for introducing fluid into and out of the fluid circuit; various kinds of plugs, and klemme, for closing and opening the flow passage and branches; a bypass for dividing the flow of body fluid for the measurement monitor; a medicine liquid administering portion; a blood port connector for connecting various kinds of circuits, an artery/vein shunt connector for connecting a circuit to an artery, a vein, or the like, and a catheter; or the like. As the medicine liquid administering portion which can be punctured with an injector needle, a porous member formed of rubber is typically used.

Further, a fluid circuit according to the present invention may be further provided with oxygen supplying means described in the following.

According to the present invention, as the measurement monitor provided in a fluid circuit for continuously measuring at least one component or one condition of the body fluid or the liquid for treatment, any one of publicly known various kinds of sensors applied to body fluid or liquid for treatment may be used. The kind, the number, and the place in the fluid circuit of the sensor can be changed depending on the purpose.

An example of such various kinds of sensors to be used in the present invention is illustrated by an NO sensor. As the NO sensor, one which can measure the NO concentration immediately and continuously in liquid is preferable. Such a sensor can be implemented by a detecting/measuring mechanism using a chemiluminescent method or an electrode method. Polarography is more preferable since the electrode can be miniaturized and the measurement accuracy can be made high. For the purpose of controlling $P_{O^2}$ in the body fluid or the liquid for treatment, an oxygen sensor is necessary. With regard to other kinds of sensors used in the present invention, any one which can measure various kinds of components in liquid immediately and continuously may be used, and sensors disclosed in the above-mentioned prior art may be used.

By using other kinds of sensors described in the above as well as the NO sensor and the oxygen sensor, functions of various kinds of such conventional sensors can be added to the present invention, which permits more detailed control. Measurement of nitrous acid ions and nitric acid ions as metabolites of NO can be used as an index of the oxygen supply effect or the like. In case a carbonic acid ion sensor is used, it can be used in preventing reactive alveolar hypoventilation caused by carbonic acid ions in the blood which are diffused through a blood processor to the dialyzing fluid. In case a pH sensor is used, the measurement can be used as an index of the acid-base balance in the liquid to be measured in monitoring acidosis or the like.

The dialyzing means used in the present invention may be any one which can remove waste products from the body fluid, and includes a flat membrane, a hollow fiber membrane, a porous member, and the like used for a hemofilter, hemodialyzer, hemofilter/dialyzer.

An apparatus for an artificial kidney according to the present invention may be any which comprises dialyzing means, a fluid circuit, and a measurement monitor, and includes a hemodialysis monitor which introduces blood from a blood vessel of a patient, makes the blood pass through a hemodialyzer using a hollow fiber membrane, and returns the blood to the patient while circulating dialyzing fluid in a surface facing a blood passage through the membrane of the hemodialyzer, a hemofilter device which does not use dialyzing fluid but filters liquid from blood with a hemofilter using a hollow fiber membrane, adds supplementary liquid to the blood, and returns the blood to the patient, and a simultaneous hemodiafilter. Further, it also includes a peritoneal dialysis system which introduces dialyzing fluid into the abdominal cavity and dialyzes blood in capillaries in the peritoneum utilizing the peritoneum, and continuous peritoneal dialyzing apparatus which automatically repeats introduction of dialyzing fluid into the abdominal cavity, making the dialyzing fluid stay in the abdominal cavity, and draining the dialyzing fluid from the abdominal cavity such as when the patient is asleep. The reason is that measurement of NO in blood and measurement of $P_{O^2}$ in arterial blood are useful and control of $P_{O^2}$ in arterial blood is advantageous also in peritoneal dialysis. In case a hollow fiber membrane comes in contact with blood, since the hollow fiber membrane is a foreign material having a large contact area, the homeostasis of the living body is disturbed. Therefore, an apparatus according to the present invention is particularly effective when applied to an apparatus for an artificial kidney using dialyzing means with a hollow fiber membrane (a hemodializer, a hemofilter, or the like).

An apparatus for an artificial kidney according to the present invention can be used in combination with a conventionally publicly known apparatus for dialysis such as a hemodialyzer, a hemodialyzing fluid supplying device, and an UFR. For example, an apparatus for an artificial kidney having an NO measurement monitor according to the present invention may be formed by using a fluid circuit according to the present invention which is a conventional blood circulation circuit for hemodialysis provided with an NO measuring portion.

The places where the above sensors are disposed are not specifically limited, although the NO sensor and the oxygen sensor are preferably provided both in an artery side circuit as the first fluid circuit and in a vein side circuit as the second fluid circuit. In a fluid circuit for an apparatus for an artificial kidney used in a blood processor as dialyzing means using a hollow fiber membrane, it is more preferable that the NO sensor is provided in a vein side circuit on the side of a blood outlet of the blood processor while the oxygen sensor is provided in an artery side circuit. Similarly, in the above fluid circuit, it is more preferable that the oxygen sensor is provided in a dialyzing fluid supply side circuit as the third fluid circuit while the NO sensor is used in a dialyzing fluid drain side circuit as the fourth circuit. In case oxygen supplying means described in the following is disposed in the fluid circuit, it is preferable that the oxygen sensor is used in a fluid outlet side circuit of the fluid circuit provided with the oxygen supplying means. Though sensors according to the present invention are preferably disposed in a fluid circuit, they may also be incorporated in a port connector connected to the dialyzer. Further, a case where the measurement monitor for continuously measuring at least one component of the body fluid or the liquid for treatment is provided in the blood processor itself also falls within the scope of the present invention.

As the method of disposing the various kinds of sensors as the measurement monitor for continuously measuring at least one component or one condition of the body fluid or the liquid for treatment according to the present invention, a method where an exposed sensor portion is fixed to a liquid circulation portion which is a part of the fluid circuit according to the present invention to be connected to the measurement monitor through wirings, a method where a sensor connecting portion is provided in a part of the fluid circuit according to the present invention and a sensor is connected to the sensor connecting portion, or the like can be used. Further, the sensors may be of a disposable type where the sensor is disposed after using one time, or may be of a reusable type. In case the sensors are of a reusable type where the sensor is repeatedly used, although the sensors themselves may directly come in contact with liquid (blood, dialyzing fluid, or the like) to be measured, if a sensor connecting portion is provided in a part of the fluid circuit according to the present invention, and, in the sensor connecting portion, a circulation portion in the fluid circuit where the main flow of the body fluid or the liquid for treatment circulates and the external are separated by a semipermeable membrane which is permeable to the gaseous component or the ionic component to be measured at a level causing no problem in continuous measurement and impermeable to bacterium, and the sensor is connected to the external side of the sensor connecting portion, there is no fear of bacterial infection of the liquid in the fluid circuit while the sensor can be reused, and the fluid circuit can be manufactured at a low price.

According to a second aspect of the present invention, in an apparatus for an artificial kidney according to the first aspect of the present invention, at least one which is selected from a group consisting of the first fluid circuit, the dialyzing means, and the second fluid circuit is provided with a treatment liquid supplying device for supplying liquid for treatment.

As the liquid for treatment used in the present invention, publicly known dialysis preparation for an artificial kidney, supplementary liquid for an artificial kidney, dialysis preparation for peritoneal dialysis, supplementary liquid for peritoneal dialysis, and the like such as bicarbonate dialyzing fluid, acetic acid dialyzing fluid, and amino acid dialyzing fluid may be used. Further, medicines including anticoagulants such as heparin sodium, anaesthetics such as halothane, ether, nitrousoxide, enflurane, isoflurane, secoflurane, intraveneous infusion such as sodium pentobarbital, general anesthetics such as ketamine hydrochloride and droperidol, albumin preparation, plasma expanders formed of preparation classified as dextran infusion, hydroxyethyl starch, dilutions for extracorporeal circulation, antihypertensive drugs such as ACE inhibitors and calcium antagonists generally used for renal failure patients, and the like may be used. These medicines can be appropriately selected depending on the purpose and can be diluted with physiological saline, if necessary, to be used.

According to the present invention, there is a measurement monitor for continuously measuring at least one component of the blood fluid or the liquid for treatment in a fluid circuit. Therefore, when, for example, the NO concentration is measured during use of an artificial kidney, hypotension in the living body is thought to be induced if the NO concentration increases. Therefore, by taking necessary steps such as circulation stop when the NO concentration reaches a predetermined control value, hypotension can be prevented. In a blood processor using a hollow fiber membrane, increase in the NO concentration is effectively observed in blood after passing through the processor as the second fluid circuit, and is also effectively observed in dialyzing fluid in the dialyzing fluid drain side circuit as the fourth fluid circuit. Further, in a peritoneal dialysis system, increase in the NO concentration is effectively observed in the dialyzing fluid drain circuit drained from the abdominal cavity as the fourth fluid circuit. The control value of the NO concentration may be appropriately set depending on the place of measurement, and is, for example, in case the blood after passing though the blood processor as the second fluid circuit is observed, 0.1–20 $\mu$M.

According to a third aspect of the present invention, an apparatus for an artificial kidney according to the first aspect of the present invention further comprises oxygen supplying means for increasing partial pressure of oxygen in arterial blood of a living body. The oxygen supplying means may supply oxygen to at least one of the first, second, third, and fourth fluid circuits, may supply oxygen to a living body under dialysis utilizing the apparatus for an artificial kidney, or may supply oxygen to the liquid for treatment itself used in the treatment.

When oxygen is supplied through the body fluid or the liquid for treatment outside the body, an air bubble type oxygenator or a membrane type oxygenator may be used as the oxygen supplying means used in the present invention. When oxygen is supplied through pulmonary respiration by the living body, an oxygen inhaler, an oxygen tent, an oxygen respiration synchronizer, an oxygen concentrator, or the like may be used. The oxygen supplying means is not limited to the above, and one which can increase $P_{O^2}$ in the blood may be used. The oxygen supplying means increases $P_{O^2}$ in the arterial blood of the patient to be adjusted and kept within a normal range.

According to the first fourth aspect of the present invention, an apparatus for an artificial kidney comprises a first fluid circuit for introducing body fluid of a living body into dialyzing means, dialyzing means for removing waste products from the body fluid, a second fluid circuit for recovering and returning the body fluid to the living body, and oxygen supplying means for increasing partial pressure of oxygen in arterial blood of the living body, and further comprises a measurement monitor for continuously measuring at least one component of the body fluid in the first fluid circuit and/or the second fluid circuit, and display means for displaying the result of comparison between a measurement value measured by the measurement monitor and a desired value.

According to the second fourth aspect of the present invention, a method of controlling the concentration of the component of body fluid of a living body uses the result of comparison of the above first fourth aspect of the present invention.

The display means used in the present invention compares a measurement value measured by the measurement monitor for monitoring a signal from the place of measurement of the component to be measured with the control value which is set in advance or which is automatically set by the apparatus depending on the situation, and, when the measurement equals the control value, displays the equality. The display means may be anything which informs the user of the equality of the measurement and the control value including lighting of a lamp, display of letters, a design, or the like on a display panel, blinking, and the like. The equality may also be made known by a buzzer or the like. Further, it is preferable that, linked with the display by the display means, the oxygen supplying means is operated or stopped to control the oxygen concentration in the living body.

The oxygen concentration in the dialyzing fluid used in the present invention may be increased as the need arises using an air bubble type oxygenator or a small-sized membrane type oxygenator formed of hollow fibers as an oxygenator. Further, as the need arises, oxygen may be added to the supplementary liquid to be used, using the above oxygenator. If oxygen is added through pulmonary respiration, selection may be made according to the purpose among the generally used oxygen supplying means including an oxygen tent, an oxygen inhaler, an oxygen respiration synchronizer, a hyperbaric oxygen chamber, an oxygen concentrator, or the like to be used. The upper limit of the adjusted $P_{O^2}$ in the arterial blood is 130% of the normal value. The lower limit may be set according to the purpose in a range which is 75% or higher of the normal value. More preferably, $P_{O^2}$ is adjusted in 90–120% of the normal value. In the present invention, by supplying controlled amount of oxygen to the arterial blood and by adjusting $P_{O^2}$ in the arterial blood in the above range, NO produced by using a conventional artificial kidney can be decreased, and, as a result, hypotension in dialysis and hypoxia can be suppressed, prevented, or treated.

According to a fifth aspect of the present invention, a quality evaluating device can evaluate action of a blood processor using dialyzing means such as a hollow fiber membrane on blood or on a living body through the blood, and can be exemplified by a quality evaluating device for dialyzing means or a quality evaluating device for dialyzing fluid. It is preferable that the quality evaluating device can reproduce the situation when actual treatment is taken or which reduces the membrane area of the hollow fiber membrane used in the blood processor or the amount of blood circulated extracorporeally. Further, the quality evaluating device may use preserved blood of man or other animals, and may use animals other than man, such as pig, rabbit, and dog. The quality evaluating device may be a quality evaluating device which does not use blood of animals. In particular, the quality evaluating device which makes the evaluation using animals other than man is preferable, since change in the living body after blood which comes in contact with the hollow fiber membrane is returned to the living body can also be evaluated.

Further, the quality evaluating device according to the present invention is useful as a device for evaluating the biocompatibility of a hemodialyzer or hemodialyzing fluid, for reviewing the action of various kinds of medicines, and for reviewing the action of physiologically active substances such as cytokine, bradykinin, endotoxin, and the like as nonclinical tests of hemodialysis under anesthesia or under no anesthesia.

Embodiment Mode of the Invention

An example of the present invention as an apparatus for an artificial kidney as a dialysis monitor using a hemodialyzer with a hollow fiber membrane is now specifically described in the following.

The dialysis monitor as an example of the present invention, artificial kidney comprises a blood pump, a dialyzing fluid pump, a pressure monitor, various kinds of controllers, and the like. Fluid circuits used in the dialysis monitor are a blood circulation circuit for circulating blood therein formed of first and second fluid circuits, a dialyzing fluid circuit for circulating dialyzing fluid therein formed of third and fourth fluid circuits, and the like. In the blood circulation circuit, component measuring portions for measuring necessary gaseous components such as NO and oxygen, or necessary ionic components such as carbonic acid ions and pH, chambers for measuring the blood pressure in the dialyzer on the inlet side and the outlet side, and the like are disposed, which are all connected to a measurement monitor of the dialysis monitor. The dynamic states of the respective components to be measured are simultaneously and continuously monitored by the measurement monitor. By operating an oxygen supplying device with an oxygen supply amount control function based on the measurement value of the measurement monitor and a-control value set in advance, the oxygen supply amount is controlled to appropriately maintain $P_{O^2}$, the NO concentration, and the like in the arterial blood.

The dialysis monitor according to the present invention has an artery side circuit as the first fluid circuit and a vein side circuit as the second fluid circuit, both as the blood circulation circuit. The artery side circuit of the blood circulation circuit connected to the artery of a patient through an artery shunt connector or a catheter has necessary elements disposed therein between the artery of the patient and the dialyzer such as an NO sensor, an oxygen sensor, a mixed injection port, a blood pressure sensor, an anticoagulant injection port, a roller pump tube, a chamber for a pressure monitor, and the like. A blood port connector at the end of the artery side circuit is connected to a blood inflow port of the hemodialyzer. Elements of the dialysis monitor in the artery side circuit include a negative pressure monitor, an anticoagulant injection pump, a blood pump, an inlet pressure monitor, an NO concentration monitor, an oxygen partial pressure monitor, and the like. The vein side circuit of the blood circulation circuit is connected to a blood outflow port of the hemodialyzer through a port connector, a chamber for capturing air bubbles, a supplementary liquid line connecting port, an NO sensor, an oxygen sensor, a mixed injection port, an air bubble detecting portion, and the like are disposed in the vein side circuit, and the vein side circuit is connected to a vein of the patient through a vein shunt connector or a catheter. Elements of the dialysis monitor in the vein side circuit include an outlet pressure monitor, an air bubble detector, a supplementary liquid injection pump, an NO concentration monitor, an oxygen partial pressure monitor, and the like.

A dialyzing fluid supply pump and a dialyzing fluid drain pump are disposed in the dialysis monitor. A dialyzing fluid supply side circuit of a dialyzing fluid circuit as the third fluid circuit has a dialyzing fluid inflow port connector connected to a dialyzing fluid inflow port of the dialyzer, a membrane type oxygenator, an oxygen sensor, and the like. A dialyzing fluid drain side circuit as the fourth fluid circuit has a dialyzing fluid outflow port connector connected to a dialyzing fluid outflow port of the dialyzer, an NO sensor, an oxygen sensor, a mixed injection port, and the like disposed therein. The mixed injection port is used in sampling a specimen and in administering medicines.

Examples of the present invention are now described in detail in the following, though the present invention is not limited thereto.

EXAMPLE 1

FIG. 1 is a schematic view illustrating Example 1 of the present invention. An arterial blood side circuit 4 as a first fluid circuit connected to an artery 2 through an artery shunt connector 3 has an NO sensor 5, an oxygen sensor 6, a blood pressure sensor 8, and a blood pump 9 disposed therein in this order along the direction of the blood flow. A port connector 10 at the end of the arterial blood side circuit 4 is connected to a blood inflow port 12 of a hemodialyzer 11 as dialyzing means. A blood outflow port 16 is connected to a vein side circuit 17 as a second fluid circuit through a port connector 13. A supplementary liquid container 18 as an example of a treatment liquid supplying device, an NO sensor 19, an oxygen sensor 20, and an air bubble detecting portion 22 are disposed in this order along the flow passage. The vein side circuit 17 is connected to a vein 24 through a vein shunt connector 23. A dialyzing fluid supplying circuit 26 as a third fluid circuit between a dialyzing fluid supplying device 25 as another treatment liquid supplying device and a dialyzing fluid inflow port 14 has an oxygen supplying device connecting joint 27 which can be connected to an oxygen supplying device 34 and an oxygen sensor 28 disposed therein. A dialyzing fluid drain circuit 29 as a fourth fluid circuit has an NO sensor 30 and an oxygen sensor 31 disposed therein. In the apparatus for an artificial kidney of the present example, the blood pressure sensor 8, the blood pump 9, a measurement monitor/recording device 32, an oxygen supply amount controller 33, and the oxygen supplying device connecting joint 27 are provided.

As the need arises, an air bubble type oxygenator or a small-sized artificial lung type oxygenator as the oxygen supplying device 34 is connected to the dialyzing fluid supplying circuit 26 to increase the concentration of oxygen contained. As the need arises, oxygen may be added to supplementary liquid supplied from the supplementary liquid container 18. The respective sensors are connected to the measurement monitor/recording device 32 through wirings (not shown). Based on data from the sensors, an oxygen inhaler 38 can be operated by the oxygen supply amount controller 33 to adjust the oxygen supply amount to the living body. Alternatively, by monitoring the values of the measurement monitor/recording device 32 and manually operating the oxygen supplying device 34 to appropriately adjust the oxygen supply amount to the third fluid circuit, $P_{O^2}$, the NO concentration, and the like as blood gaseous components in the arterial blood can be made appropriate. The oxygen supplying device 34 may be controlled by the oxygen supply amount controller 33.

EXAMPLE 2

Pig Extracorporeal Circulation Circuit for Evaluating Hemodialyzer

Figure 2:
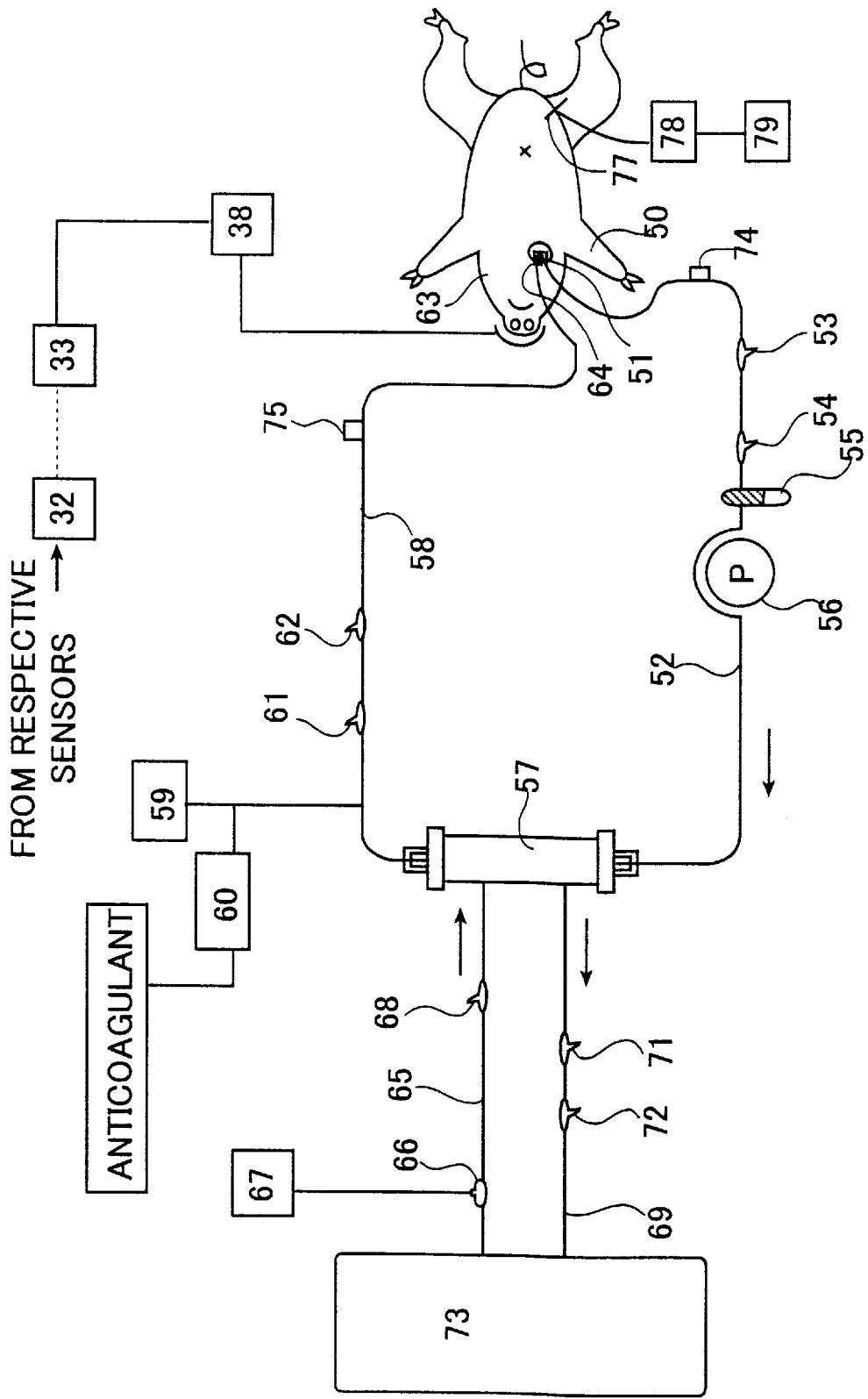
FIG. 2 is a structural view as a whole, illustrating Example 2 according to the present invention.

FIG. 2 is a conceptual view of a quality evaluating device of a hemodialyzer using an apparatus for an artificial kidney formed of an extracorporeal blood circulation circuit using a castrated pig (weight: 50 Kg) 63 and an oxygen supplying device. In the experiment, a hemodialyzer 57 using a commercially available cellulose hollow fiber membrane type hemodialyzer (membrane area: 1.5 m$^2$), an artery side circuit 52 as a first fluid circuit in a blood circulation circuit, and a vein side circuit 58 as a second fluid circuit were primed by connecting a physiological saline container to a mixed injection port 74, driving a blood pump 56, and filling 500 ml of physiological saline at a flow rate of 100 ml/min to perform cleaning. Then, the vein side circuit 58 is closed, 500 ml of physiological saline was introduced into the hemodialyzer, complete filtering was performed, and the dialyzing fluid side was cleaned. After that, a dialyzing fluid circuit was connected to a dialyzing fluid inflow port and outflow port, and cleaning with the dialyzing fluid was performed for ten minutes. Then, the physiological saline container was replaced by 1 IU/ml heparinized physiological saline to prime the hemodialyzer 57, and the blood circulation circuit including the artery side circuit 52 and the vein side circuit 58.

An artery side catheter 51, an NO sensor 53, a mixed injection port 74, an oxygen sensor 54, a blood pressure sensor 55, and a blood pump 56 were disposed in the artery side circuit 52 of the blood circulation circuit. A supplementary liquid line having a supplementary liquid container 59, an NO sensor 61, an oxygen sensor 62, a mixed injection port 75, and a vein side catheter 64 were provided in the vein side circuit 58. In a dialyzing fluid supplying circuit 65 as a third fluid circuit which is connected to a dialyzing fluid supplying device 73 which is a treatment liquid supplying device, a joint 66 for supplying oxygen was connected to an oxygenator 67, and an oxygen sensor 68 was disposed. In a dialyzing fluid drain circuit 69 as a fourth fluid circuit, an NO sensor 71 and an oxygen sensor 72 were disposed. The respective sensors were connected to a measurement monitor/recording device 32 through wirings not shown. An oxygen supply amount controller 33 and an oxygen inhaler 38 were provided for making appropriate $P_{O^2}$ and the NO concentration in the arterial blood based on data from the sensors. The measurement monitor/recording device 32 has a measurement value display panel and a setting dial for setting an upper limit value and a lower limit value as control values. When a control value equals the measurement, the measurement display on the measurement display panel blinks, and a buzzer is sounded. In the apparatus for dialysis of the present example, the blood pressure sensor 55, the blood pump 56, the measurement monitor/recording device 32, a syringe pump 60, a continuous pressure monitor 79, the oxygen supply amount controller 33, and an oxygenator 67 are provided.

With regard to the anesthetic management, atropine sulfate (Tanabe Seiyaku Co., Ltd.) and Stresnil (Sankyo Company, Ltd.) which is a sedative for pig were mixed and administered in the muscle as preanesthetic medication, and fifteen minutes later, a predetermined amount of ketamine was administered in the muscle. As continuous anesthesia after that, laughing gas and halothane (Takeda Chemical Industries, Ltd.) as an inhalation anesthetic together with oxygen were used through an inhalation anesthesia apparatus. Under anesthesia, the common carotid artery 50 and the common jugular vein 63 of the pig were surgically detached and secured. Then, the vein side catheter 64 and the artery side catheter 51 primed using 1 IU/ml heparinized physiological saline were inserted in and fixed to the vessels, respectively, by cutdown.

Then, after heparin of 75 IU/Kg was initially administered through the fixed vein side catheter 64, connection was made to the vein side circuit 58, and the artery 50 was connected to the artery side catheter 51 of the artery side circuit 52. Then, the blood pump 56 was operated at the flow rate of 100 ml/min and the flow rate was increased by 10 ml/min every minute such that the final blood flow rate (Qb)=200 ml/min. The dialyzing fluid flow rate and the-water removing speed were set to be 500 ml/min and 500 ml/hr, respectively. During the extracorporeal circulation, heparin was continuously administered at the administration amount of 1600 IU/hr from the syringe pump 60 to the vein side circuit 58.

With regard to the blood pressure measurement of the pig during the blood circulation, a femoral artery 77 was exposed and a catheter was inserted in and fixed to the femoral artery 77 by cutdown to secure a blood pressure measurement line. Pressure sensors not shown which are pressure transducers were disposed to an artery side circuit 52 and a vein side circuit 58 between the blood pump 56 and the hemodialyzer 57 of the extracorporeal circulation circuit and disposed in the femoral artery 77, respectively, to record the blood pressure using the continuous pressure monitor 79.

Measurement of NOx in the urine was made by sampling the urine as time passes through a catheter inserted in a ureter by abdominal section, and by using an NOx measurement kit. With regard to measurement of gas partial pressure and ion concentration in the blood and in the dialyzing fluid, measurements from the sensors disposed in the extracorporeal circulation circuit were recorded in the measurement monitor/recording device 32, and based on the obtained data, the oxygen supply amount was adjusted to keep the partial pressure of oxygen in artery and the NO concentration in the blood in a normal range. With regard to the partial pressure of carbon dioxide $P_{CO_2}$ in the blood, the blood was sampled intermittently from the blood circuit, and the measurement was made using a blood gas analyzer (ABL50 by Radiometer Kabushiki Kaisha).

Using the above-described pig extracorporeal circulation circuit, dialyzing fluid (Kindery AF-2 manufactured by Fuyo Yakuhin Kabushiki Kaisha) was made to circulate in the dialyzing fluid circuit, dialysis was performed, and the influence of the dialysis using the dialyzer with the hollow fiber membrane on the blood gas partial pressures of the living body was measured. The result was that decrease in the $P_{O_2}$ value in the arterial blood from the initial value of 250 mmHg to 158 mmHg and decrease in the $P_{CO_2}$ value in the arterial blood from the initial value of 65 mmHg to 10 mmHg were observed. When oxygen was inhaled from the nasal cavity, the $P_{O_2}$ value in the arterial blood increased to 243–255 mmHg while the $P_{CO_2}$ value in the arterial blood returned to 61–65 mmHg, which almost equals the initial value.

NOx in the urine reached its peak when fifteen minutes passed from the start of the dialysis. However, hypotension was not observed, which suggests that the adjustment of the partial pressure of oxygen in artery facilitates the metabolism to NOx of excess NO in the blood which affects the blood pressure.

EXAMPLE 3

Figure 3:
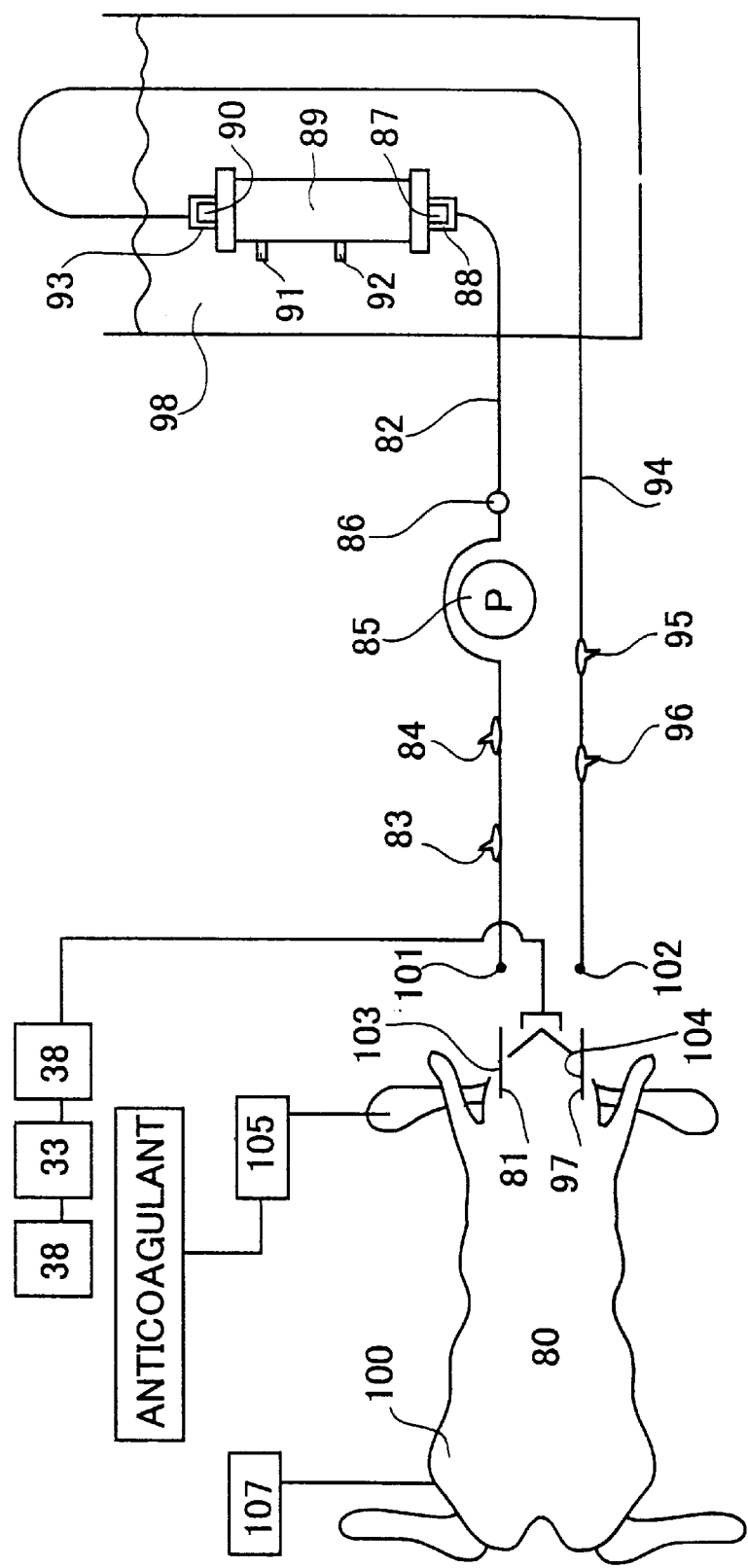
FIG. 3 is a structural view as a whole, illustrating Example 3 according to the present invention.

Production of Rabbit Extracorporeal Circulation Circuit System for Evaluating Hemodialyzer FIG. 3 is a conceptual view of a quality evaluating device of a hemodialyzer using an apparatus for an artificial kidney formed of an extracorporeal blood circulation circuit using a rabbit 80 and an oxygen supplying device. A hemodialyzer 89 as dialyzing means using a commercially available cellulose hollow fiber membrane type hemodialyzer (membrane area: 1.5 m²) was primed by, after the hemodialyzer 89 was connected to the blood circulation circuit to complete the circuit, connecting a physiological saline container to a catheter connecting port 101 of an artery side circuit 82 as a first fluid circuit, operating a blood pump 85, and draining physiological saline from a catheter connecting port 102 of a vein side circuit 94 as a second fluid circuit. The blood flow passage side of the hemodialyzer was cleaned by injecting 500 ml of physiological saline at a flow rate of 50 ml/min from a catheter connecting port 101 and draining the cleaning liquid from a catheter connecting port 102 of a vein side circuit 94. The dialyzing fluid side of the hemodialyzer 89 was cleaned by injecting 500 ml of physiological saline from a dialyzing fluid inflow port 91.

Then, the physiological saline in the hemodialyzer and in the blood circulation circuit was displaced by a plasma substitute by means of injecting 250 ml of the plasma substitute from the catheter connecting port 101. After the displacement, the catheter connecting port 101 was connected to an artery 81 of the rabbit while the catheter connecting port 102 was connected to a vein 97 of the rabbit. In order to make small the temperature difference between the blood flowing through the extracorporeal circulation circuit and the body of the animal, the hemodialyzer 89 was put in a thermostatic bath 98 to keep the temperature of the hemodialyzer 89 at 38–39° C.

The back of the rabbit (female, weight: 2.2 Kg) was fixed to a Kitajima fixing table. After the fur in the area of the operation was shaved, the common carotid artery 81 and the common jugular vein 97 were surgically detached and secured. Then, indwelling catheters having the inside diameter of 1.65 mm primed using 5 IU/ml heparinized physiological saline were inserted by cutdown to be fixed to an artery side catheter 103 and a vein side catheter 104, respectively, by ligature. Then, heparinized physiological saline was given through the fixed artery side catheter 103. Five minutes later, the artery side catheter 103 was connected to the catheter connecting port 101 of the blood circulation circuit the inside of which had already been displaced by the plasma substitute, the vein side catheter 102 was connected to the catheter connecting port 104, and the blood pump 85 was driven to start the extracorporeal circulation. With regard to the administration amount of heparin in the extracorporeal circulation, heparin at the rate of 7 IU/kg/hr was continuously injected from a needle indwelling in a rabbit auricular vein 99 using a syringe pump (STC-525 manufactured by TERUMO Corporation) 105. The extracorporeal circulation blood flow rate was set to be 20 ml/min which was the maximum circulation amount without blood pressure fluctuation, and the circulation was performed for 15–30 minutes.

With regard to the blood pressure measurement, an indwelling catheter having the inside diameter of 1.65 mm was inserted from a femoral artery 100, fixed by ligature, and then connected to a pressure transducer (TP-00T manufactured by Nihon Koden Kabushiki Kaisha), and the measurement was recorded by a pressure monitor 107.

With regard to the measurement of nitric oxide (NO) in the blood, an NO sensor 83 of an artery side circuit 82 having an electrode for measuring NO and an NO sensor 95 disposed in a vein side circuit 94 and having an electrode for measuring NO were connected through wirings not shown to a nitric oxide measuring device (NO-501 manufactured by Inter Medical Co., LTD.) incorporated in a measurement monitor 31. With regard to the measurement of $P_{O_2}$ in the blood, an oxygen electrode 83 for the artery side circuit and an oxygen electrode 96 for the vein side circuit were connected through wirings not shown to oxygen partial pressure measuring device (P-02-100DW manufactured by Inter Medical Co., LTD.) incorporated in the measurement monitor 31. The measurement was recorded by an external recorder which is not shown.

In the quality evaluating device of the present example, the blood pump 85, the measurement monitor 31, the syringe pump 105, the pressure monitor 107, and the like are provided.

As a result of the above experiment, the arterial blood NO concentration in the extracorporeal circulation system of the rabbit was measurable in the range of 0–30 $\mu$M. The arterial blood NO concentration in the extracorporeal circulation system of the rabbit under no anesthesia (n=16) was in the range of 1–9 $\mu$M. $P_{O_2}$ in the arterial blood was 60–90 mmHg.

FIGS. 4–9 illustrate an example of the measurement result. It is to be noted that the time in the figures is zero when the artery side blood flows in the hemodialyzer, and "IN" denotes artery side circuit and "OUT" denotes vein side circuit.

Figure 4:
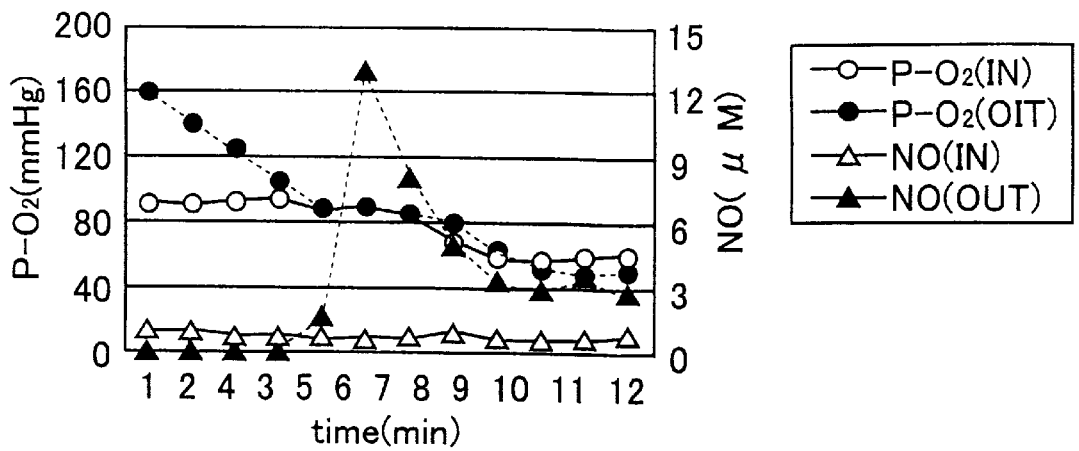
FIG. 4 is a graph of the result of measurement of $P_{O^2}$ and the NO concentration which is made with regard to a measurement example of Example 3.
Figure 5:
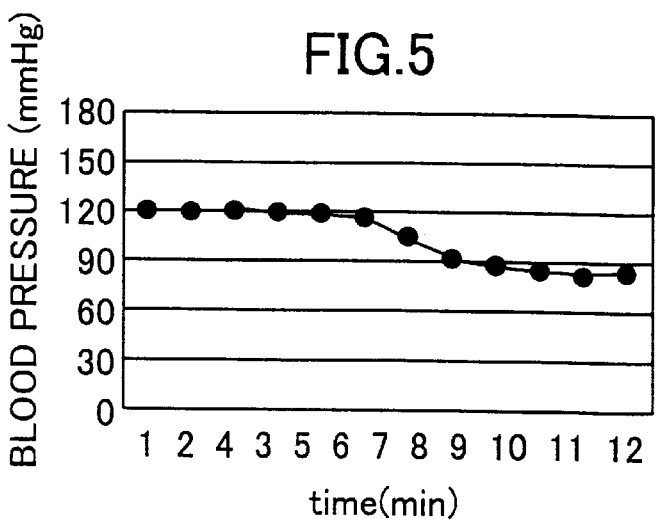
FIG. 5 is a graph of the result of measurement of the blood pressure in the case of FIG. 4.

FIGS. 4 and 5 illustrate $P_{O^2}$ and the NO concentration and the rabbit femoral artery pressure, respectively, of a measurement example where hypotension was observed. When five minutes passed, the NO concentration in the vein side blood started to increase, and a little later, hypotension was observed.

Figure 6:
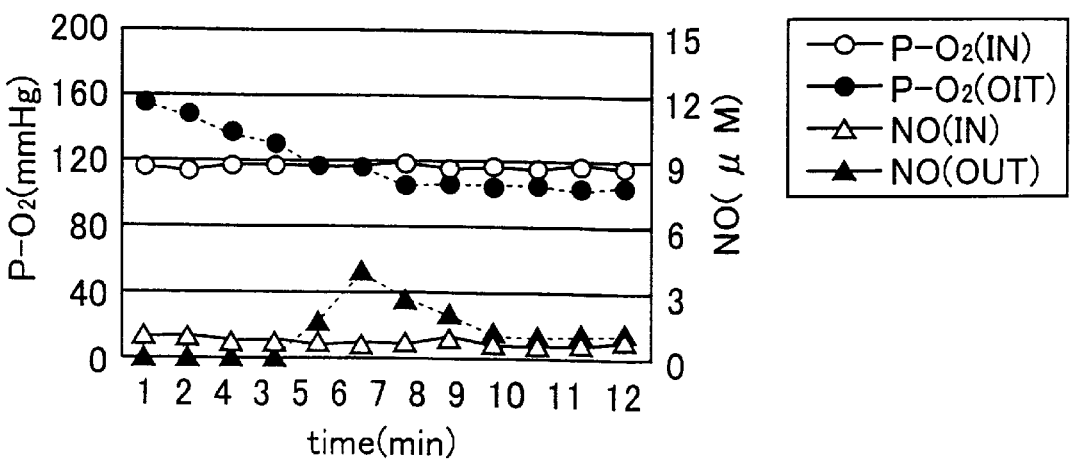
FIG. 6 is a graph of the result of another measurement of $P_{O^2}$ and the NO concentration which is made with regard to a measurement example of Example 3.

FIGS. 6 and 7 illustrate $P_{O^2}$ and the NO concentration and the rabbit femoral artery pressure, respectively, of a measurement example where a hemodialyzer of the same lot as that of the one used in the case of FIGS. 4 and 5 was used, and from the beginning of the circulation, the rabbit inhaled oxygen using an oxygen inhaler 38 the oxygen concentration of which was controlled by an oxygen supply amount controller 33. $P_{O^2}$ in the arterial blood was controlled to be 110–115 mmHg. When five minutes passed, a little amount of increase in the NO concentration in the vein side blood was observed, but almost no decrease in the blood pressure was observed.

FIGS. 8 and 9 illustrate $P_{O^2}$ and the NO concentration and the rabbit femoral artery pressure, respectively, of a measurement example where another hemodialyzer was used and no oxygen was supplied. For twelve minutes after the blood flowed in the hemodialyzer, fluctuation in the NO concentration was not observed, and the blood pressure was almost constant.

As described in the above, according to the present invention, the quality of a hemodialyzer using a hollow fiber membrane could be evaluated. More quantitative and detailed evaluation was made possible compared with a case of a conventional evaluation system where the evaluation was made by observing the blood pressure fluctuation of a rabbit. Further, it was made clear that NO produced in a hemodialyzer decreased the partial pressure of oxygen in the blood. On the other hand, by adjusting the oxygen supply amount when the NO concentration in the blood increased, the partial pressure of oxygen in arterial blood value and the blood pressure could be made normal. The present invention has sufficient effects when the increase in the NO concentration in the blood is steep but the NO concentration does not exceed seven times as much as a normal value.

As described in detail in the above, according to the present invention, an apparatus which, by simultaneously monitoring the dynamic states of gaseous components and ionic components included in an extracorporeal circulation circuit liquid during artificial dialysis, can promptly deal with onset and development of diseases such as blood pressure drop and hypoxia associating with the artificial dialysis, and a novel method of evaluating a hemodialyzer using such an apparatus and hemodialyzing fluid can be provided.

What is claimed is:

1. An apparatus for an artificial kidney comprising:
   a first fluid circuit for introducing body fluid into dialyzing means;
   dialyzing means for removing waste products from the body fluid; and
   a second fluid circuit for recovering the body fluid, further comprising a measurement monitor for continuously measuring nitric oxide (NO) or nitric oxide oxydant (NOx) of the body fluid in said first fluid circuit and/or said second fluid circuit to detect a possibility of hypotension or hypoxia associated with artificial dialysis.

2. An apparatus for an artificial kidney as claimed in claim 1, further comprising:
   oxygen supplying means for increasing partial pressure of oxygen in arterial blood of a living body.

3. An apparatus for an artificial kidney as claimed in claim 2, wherein said oxygen supplying means is at least one which is selected from a group consisting of an air bubble type oxygenator, a membrane type oxygenator, an oxygen inhaler, an oxygen tent, an oxygen respiration synchronizer, and an oxygen concentrator.

4. An apparatus for an artificial kidney as claimed in claim 1, characterized in that said dialyzing means is a blood processor using a hollow fiber membrane, and/or said liquid for treatment is dialyzing fluid.

5. A dialyzing fluid supplying device comprising a third fluid circuit for introducing dialyzing fluid to the apparatus for an artificial kidney of claim 1, and a fourth fluid circuit for recovering the dialyzing fluid from the apparatus for an artificial kidney of claim 1, further comprising a measurement monitor for continuously measuring nitric oxide (NO) or nitric oxide oxydant (NOx) of the dialyzing fluid in the third fluid circuit and/or the fourth fluid circuit.

6. An apparatus for an artificial kidney as claimed in claim 1, wherein the measurement of nitric oxide (NO) or nitric oxide oxydant (NOx) is measured by an NO electrode.

7. An apparatus for an artificial kidney comprising:
   a first fluid circuit for introducing body fluid of a living body into dialyzing means;
   dialyzing means for removing waste products from the body fluid;
   a second fluid circuit for recovering and returning the body fluid to the living body; and
   oxygen supplying means for increasing partial pressure of oxygen in arterial blood of the living body,
   further comprising a measurement monitor for continuously measuring nitric oxide (NO) or nitric oxide oxydant (NOx) of the body fluid in said first fluid circuit and/or said second fluid circuit to detect a possibility of hypotension or hypoxia associated with artificial dialysis, and display means for displaying the result of comparison between a measurement value measured by said measurement monitor and a desired value.

8. A quality evaluating device for dialyzing comprising:
   a first fluid circuit for introducing body fluid into dialyzing means;
   dialyzing means for removing waste products from the body fluid; and
   a second fluid circuit for recovering the body fluid, further comprising a measurement monitor for continuously measuring nitric oxide (NO) or nitric oxide oxydant (NOx) of the body fluid in said first fluid circuit and/or said second fluid circuit and by being capable of evaluating the quality of said dialyzing means.

9. A quality evaluating device for dialyzing fluid comprising:
   a first fluid circuit for introducing body fluid into dialyzing means;
   dialyzing means for removing waste products from the body fluid; and
   a second fluid circuit for recovering the body fluid, further comprising a measurement monitor for continuously measuring nitric oxide (NO) or nitric oxide oxydant (NOx) of the body fluid in said first fluid circuit and/or said second fluid circuit, optional oxygen supplying means, and a dialyzing fluid supplying device for supplying dialyzing fluid to said dialyzing means, and by being capable of evaluating the quality of the dialyzing fluid.

10. A circuit or a device as claimed in claim 9, respectively, wherein said oxygen supplying means is at least one which is selected from a group consisting of an air bubble type oxygenator, a membrane type oxygenator, an oxygen inhaler, an oxygen tent, an oxygen respiration synchronizer, and an oxygen concentrator.

11. A dialyzing fluid supplying device comprising:

an introducing fluid circuit for introducing dialyzing fluid; and a recovery fluid circuit for recovering the dialyzing fluid, further comprising a measurement monitor for continuously measuring nitric oxide (NO) or nitric oxide oxydant (NOx) of the dialyzing fluid in said introducing fluid circuit and/or said recovery fluid circuit.

12. A method of controlling the concentration of nitric oxide (NO) or nitric oxide oxydant (NOx) of body fluid of a living body by comprising a first fluid circuit for introducing body fluid of a living body into dialyzing means, dialyzing means for removing waste products from the body fluid, a second fluid circuit for recovering and returning the body fluid to the living body, and oxygen supplying means for increasing partial pressure of oxygen in arterial blood of the living body, further comprising a measurement monitor for continuously measuring nitric oxide (NO) or nitric oxide oxydant (NOx) of the body fluid in the first fluid circuit and/or the second fluid circuit, and by comparing a measurement value measured by the measurement monitor with a desired value.

13. A dialyzing fluid supplying device for peritoneal dialyzing comprising an introducing fluid circuit for introducing dialyzing fluid to an abdominal cavity, a recovery fluid circuit for recovering the dialyzing fluid from the abdominal cavity, and a measurement monitor for continuously measuring nitric oxide (NO) or nitric oxide oxydant (NOx) of the dialyzing fluid in the introducing fluid circuit and/or the recovery fluid circuit to detect a possibility of hypotension or hypoxia associated with artificial dialysis.

* * * * *